US008357190B2

(12) United States Patent
Fearn et al.

(10) Patent No.: US 8,357,190 B2
(45) Date of Patent: Jan. 22, 2013

(54) LAPAROSCOPIC VASCULAR ACCESS

(75) Inventors: Shirley Jane Fearn, Lesmurdie (AU); David Ernest Hartley, Subiaco (AU); Michael Lawrence-Brown, City Beach (AU)

(73) Assignees: Cook Medical Technologies LLC, Bloomington, IN (US); William A. Cook Australia Pty. Ltd. (AU)

( * ) Notice: Subject to any disclaimer, the term of this patent is extended or adjusted under 35 U.S.C. 154(b) by 854 days.

(21) Appl. No.: 11/429,684

(22) Filed: May 8, 2006

(65) Prior Publication Data

US 2006/0282155 A1 Dec. 14, 2006

Related U.S. Application Data

(60) Provisional application No. 60/679,612, filed on May 10, 2005.

(51) Int. Cl.
*A61F 2/06* (2006.01)
(52) U.S. Cl. ................. 623/1.11; 623/1.13; 623/1.23
(58) Field of Classification Search .............. 623/1.13, 623/1.12, 1.11, 1.15, 1.16, 1.23; 606/192, 606/144, 108, 223; 604/107, 95
See application file for complete search history.

(56) References Cited

U.S. PATENT DOCUMENTS

| 4,830,003 | A | * | 5/1989 | Wolff et al. | 606/191 |
|---|---|---|---|---|---|
| 5,697,941 | A | * | 12/1997 | Christy | 606/144 |
| 5,817,123 | A | * | 10/1998 | Kieturakis et al. | 606/192 |
| 6,695,875 | B2 | * | 2/2004 | Stelter et al. | 623/1.13 |
| 2002/0151953 | A1 | * | 10/2002 | Chobotov et al. | 623/1.11 |
| 2002/0156522 | A1 | * | 10/2002 | Ivancev et al. | 623/1.13 |
| 2003/0088305 | A1 | * | 5/2003 | Van Schie et al. | 623/1.12 |
| 2003/0225446 | A1 | * | 12/2003 | Hartley | 623/1.11 |

* cited by examiner

*Primary Examiner* — Ryan Severson
*Assistant Examiner* — Tin Nguyen
(74) *Attorney, Agent, or Firm* — Brinks Hofer Gilson & Lione

(57) ABSTRACT

A laparoscopic vascular conduit arrangement has an elongate graft tube (1, 10) which is placed through a body cavity into a body vessel using a laparoscopic port sheath (70) with a distal valve (73) and a second sheath (80) with distal valve (86, 87). The graft tube (1, 10) extends through the laparoscopic port sheath so that the distal end (108) of the graft tube extends out of its valve and the proximal end of the graft tube extends out of the proximal end of the laparoscopic port sheath. The second sheath (80) is deployed into the distal end (108) of the graft tube (1, 10) such that the first valve (73) seals around the graft tube and the second sheath (84). The proximal end of the graft tube can be deployed into the vessel of the body to allow access into the vessel through the graft tube via the second valve. The conduit can be removed after use or used to provide vascular bypass.

8 Claims, 17 Drawing Sheets

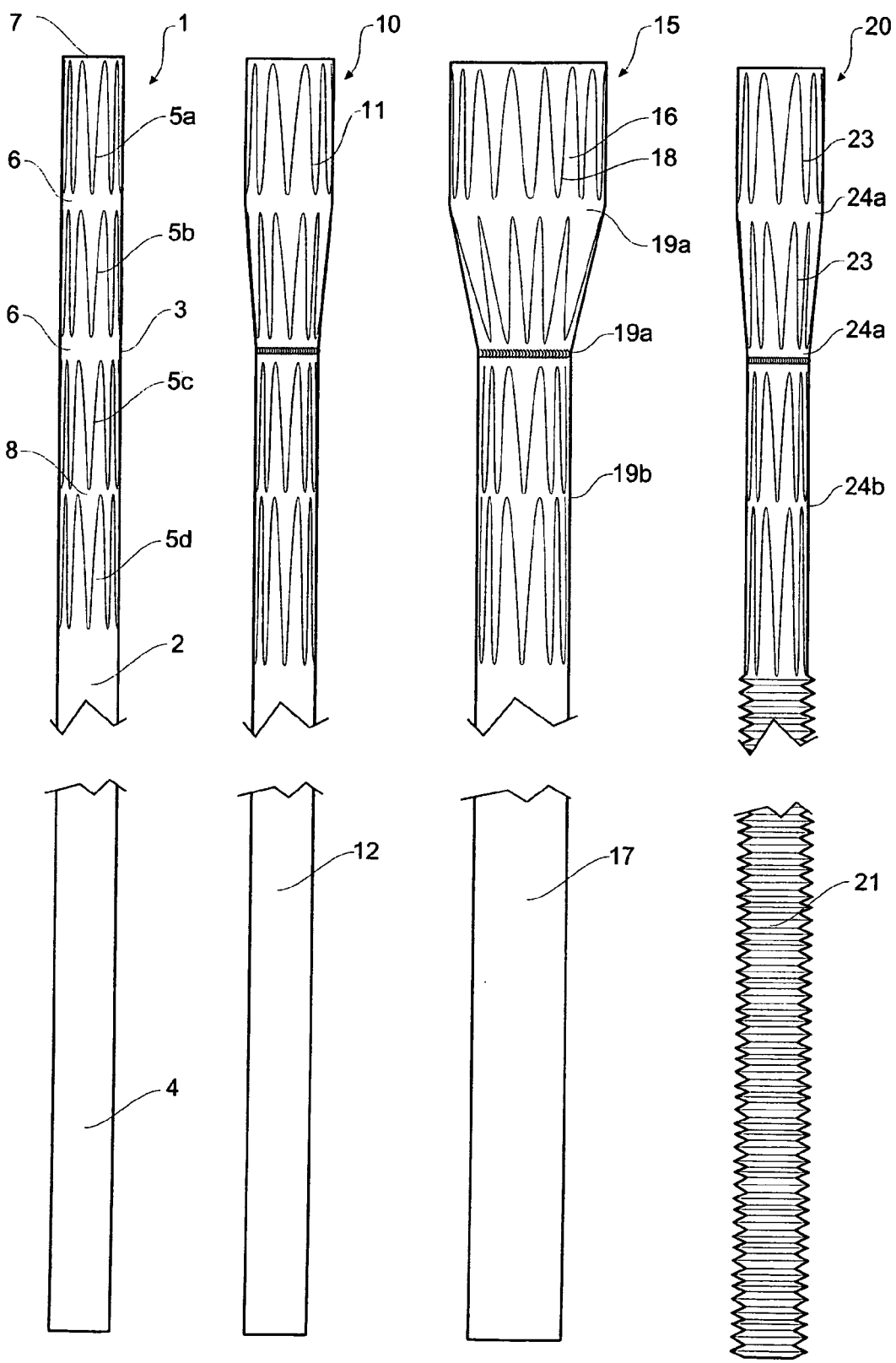

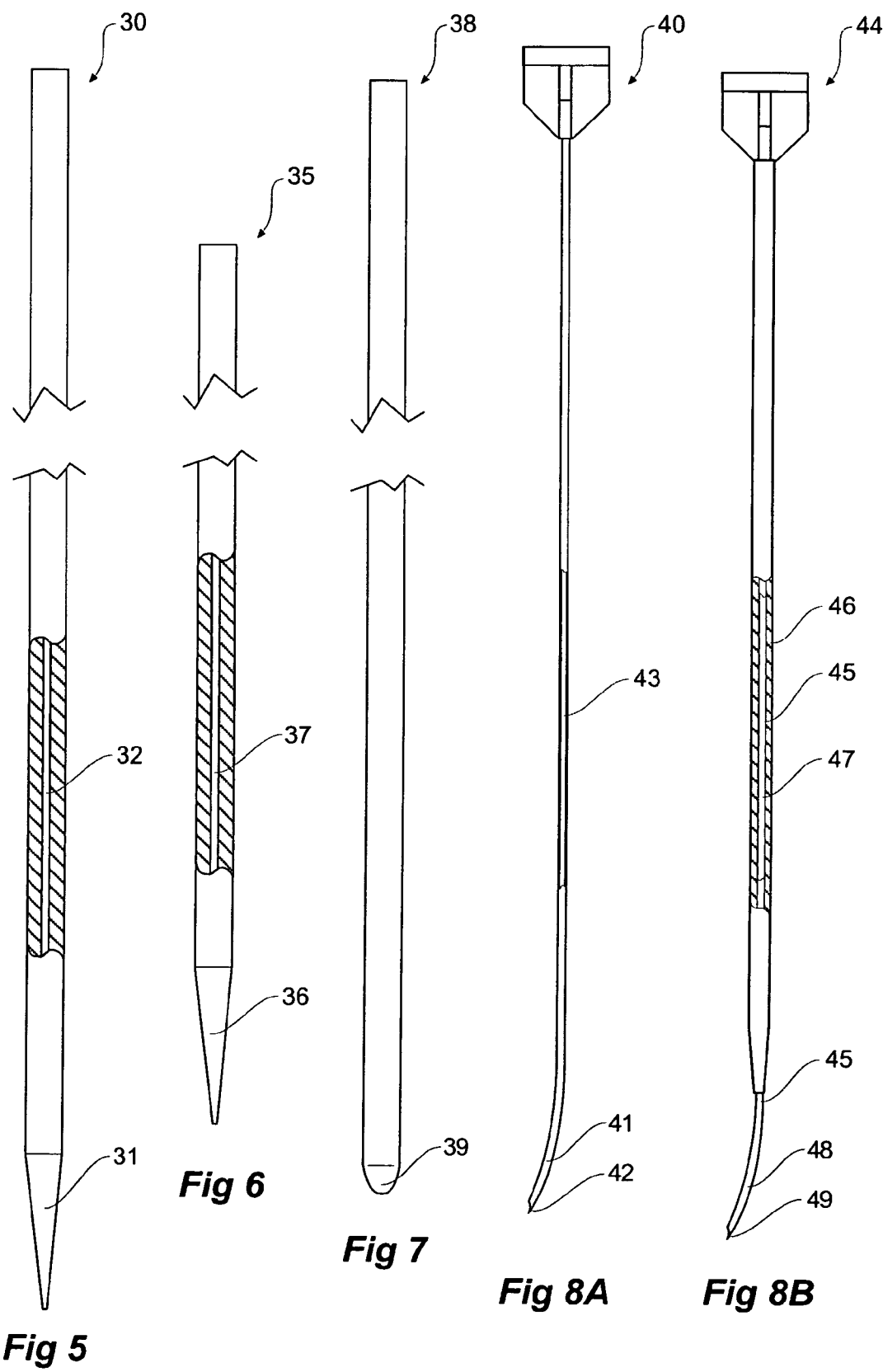

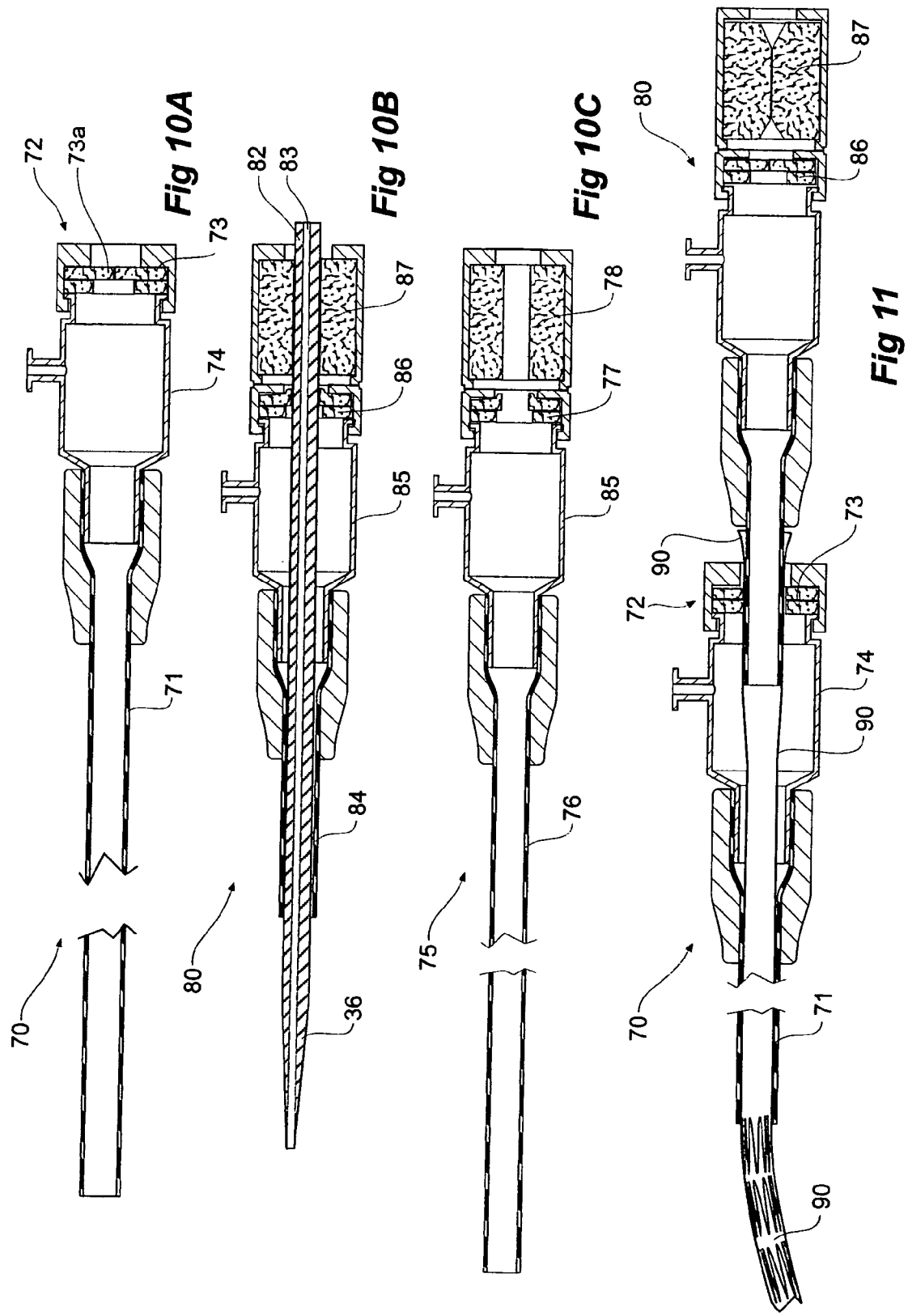

LAPAROSCOPIC VASCULAR ACCESS

CROSS-REFERENCE TO RELATED APPLICATIONS

This application claims priority of provisional application Ser. No. 60/679,612, filed May 10, 2005.

TECHNICAL FIELD

This invention relates to a medical device and more particularly to a medical device and arrangement for performing laparoscopic vascular access.

BACKGROUND OF THE INVENTION

Endovascular access using arteries close to the surface of the skin of a patient has been well practised in recent years. The Seldinger method of access to the aorta through a femoral and iliac artery has been well practised but there are problems when the femoral and iliac arteries are convoluted, too small for access or occluded and in such situations a physician must resort to open surgery.

Endoscopic techniques to provide access into the various body cavities are also well known. It is an object of this invention to provide a system and equipment for endoscopic controlled and guided vascular access and in particular laparoscopic controlled and guided vascular access into the abdominal cavity. Alternatively, thoracoscopic controlled and guided access may be used into the thoracic cavity of a patient for heart vessel surgery.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form therefore, the invention is said to reside in a laparoscopic vascular conduit arrangement comprising, an elongate graft tube having a proximal end and a distal end, the proximal end having at least one self expanding stent affixed thereto to keep the proximal end open and an elongate distal unstented portion, a laparoscopic port sheath having a first access port at a distal end thereof, a second sheath having a second access port at a distal end thereof, the graft tube extending through the laparoscopic port sheath such the distal end of the graft tube is extendable out of the first access port and the proximal end of the graft tube is extendable out of the proximal end of the laparoscopic port sheath, and the second sheath being deployable into the distal end of the graft tube such that the first access port seals around the graft tube and the second sheath, whereby the proximal end of the graft tube can be deployed into a vessel of the body to allow access into the vessel through the graft tube via the second access port.

Preferably the elongate graft tube is Dacron or PTFE or any other suitable biocompatible material.

In one embodiment the graft tube has four self expanding stents at the proximal end thereof, with gaps therebetween, wider gaps between the first and second stents and the second and third stents and a narrower gap between the third and fourth stent. Preferably the stents are on the inside of the graft material tube.

The graft tube may have a diameter of from 12 to 16 mm in region of first stent, tapering to 6 to 10 mm in the region of second stent and continuing at 6 to 10 mm diameter to distal end. Alternatively the graft tube may be adapted for placement into the aorta to seal therein and have a diameter of from 12 to 40 mm in region of first stent, tapering to 6 to 20 mm in region of second stent and continuing at 6 to 20 mm diameter to its distal end.

The first access port may have self sealing valve and the second access port may have a manually operable sealing valve and a self sealing valve.

In a further form the invention comprises a laparoscopic conduit comprising an elongate graft tube having a proximal end and a distal end, the proximal end having at least two self expanding stents affixed thereto to keep the proximal end open and a gap between the at least two stents to provide a sealing region to seal through an aperture in a vessel wall and an elongate distal unstented portion.

In one embodiment the graft tube has four self expanding stents at the proximal end thereof, with gaps therebetween, wider gaps between the first and second stents and the second and third stents and a narrower gap between the third and fourth stent. Preferably the stents are on the inside of the graft material tube.

The stents may be expandable stent being either balloon or mechanically expandable stents or self expanding stents.

The elongate distal unstented portion may comprise a corrugated biocompatible graft material.

In a further form the invention comprises a laparoscopic vascular access arrangement to provide temporary vascular access comprising, a laparoscopic port sheath having an first access port at a distal end thereof, a second sheath of lesser diameter to fit through the laparoscopic port sheath and having a second access port at a distal end thereof, and the second sheath being extendable through the laparoscopic port sheath such the distal end of the second sheath is extendable out of the first access port and the proximal end of the second sheath is extendable out of the proximal end of the laparoscopic port sheath, whereby the proximal end of the second sheath can be deployed into a vessel of the body to allow access into the vessel through the graft tube via the second access port.

In a further form the invention comprises a deployment device for a laparoscopic conduit, the laparoscopic conduit comprising an elongate graft tube having a proximal end and a distal end, the proximal end having at least two self expanding stents affixed thereto to keep the proximal end open, a gap between the at least two stents to provide a sealing region to seal through an aperture in a vessel wall and an elongate distal unstented portion, the deployment device comprising a pusher catheter, a guide wire catheter extending from the pusher catheter to a nose cone dilator and a pusher catheter extension of lesser diameter than the pusher catheter extension in use to extend through the elongate distal unstented portion of the elongate graft tube to bear against the distal most self expanding stent, the laparoscopic conduit in use being retained in a contracted condition between the distal end of the nose cone dilator and the proximal end of the pusher catheter.

Preferably the deployment device further comprises a sheath surrounding the laparoscopic conduit and the pusher catheter and leaving an annular space between the pusher catheter extension and the sheath for the elongate distal unstented portion.

Preferably the sheath is retractable to release the laparoscopic conduit and the pusher catheter extension prevents distal movement of the laparoscopic conduit during the retraction.

The sheath may be an elongate flexible sheath such as a Flexor® sheath commercially available from Cook Incorporated, Bloomington Ind.

Preferably the elongate distal unstented portion of the laparoscopic conduit comprises a corrugated biocompatible material portion and the corrugated biocompatible material portion is retained in a contracted condition in the annular space between the pusher catheter extension and the sheath.

The graft tube may have a diameter of from 12-40 mm in region of first stent, tapering to 6-20 mm in region of second stent and continuing at 6-20 mm diameter to distal end.

In a further form the invention comprises a kit of parts for performing vascular access laparoscopically, the kit of parts comprising;

an elongate curved hollow needle,
a guide wire,
a laparoscopic port sheath,
a blunt obturator of a diameter to extend through the laparoscopic port sheath,
a smaller diameter sheath, and
a sharp ended obturator of a diameter to extend through the smaller diameter sheath.

Preferably the laparoscopic port sheath comprises an elongate flexible sheath having a proximal end and a distal end and an access port at the distal end, the access port having a sealing valve therein.

Preferably the smaller diameter sheath comprises an elongate flexible sheath having a proximal end and a distal end and an access port at the distal end, the access port having a self sealing valve and a manually operable valve therein.

The kit of parts can further include a laparoscopic conduit loaded onto a delivery device.

Preferably the laparoscopic conduit comprises an elongate graft tube having a proximal end and a distal end, the proximal end having at least two self expanding stents affixed thereto to keep the proximal end open and a gap between the at least two stents to provide a sealing region to seal through an aperture in a vessel wall and an elongate distal unstented portion.

Preferably the delivery device comprises a pusher catheter, a guide wire catheter extending from the pusher catheter to a nose cone dilator and a pusher catheter extension of lesser diameter than the pusher catheter extension in use to extend through the elongate distal unstented portion of the elongate graft tube to bear against the distal most self expanding stent, the laparoscopic conduit in use being retained between the distal end of the nose cone dilator and the proximal end of the pusher catheter.

In one embodiment the elongate curved hollow needle can comprise a reinforcing body surrounding the needle. The reinforcement can comprise a catheter around the needle extending along a substantial proportion of the needle. The reinforcement not only provides strength and support for the needle as it is extended out beyond the laparoscopic port sheath but it also assists in obtaining a seal between the needle and the hemostatic valve at the distal end of the laparoscopic port sheath.

BRIEF DESCRIPTION OF THE DRAWING

This then generally describes the invention but to assist with understanding reference will now be made to preferred embodiments of the invention with the assistance of drawings.

In the drawings:

FIG. 1 shows a first embodiment of a laparoscopic conduit according to the present invention;

FIG. 2 shows an alternative embodiment of a laparoscopic conduit according to the present invention;

FIG. 3 shows a still further embodiment of a laparoscopic conduit according to the present invention;

FIG. 4 shows a further embodiment of a laparoscopic conduit which incorporates a corrugated unstented portion according to the present invention;

FIG. 5 shows a obturation device with a tapered distal end suitable for use with the present invention;

FIG. 6 shows a short obturator with a tapered distal end suitable for use with the present invention;

FIG. 7 shows an obturator with a blunt distal end suitable for use with the present invention;

FIG. 8A shows one embodiment of a long curved needle suitable for use with the present invention;

FIG. 8B shows an alternative embodiment of a long curved needle suitable for use with the present invention;

FIG. 10A shows a laparoscopic access sheath according to one embodiment of the present invention;

FIG. 10B shows a second laparoscopic access sheath loaded with a short tapered obturator and suitable for the present invention;

FIG. 10C shows a third access sheath suitable for the present invention;

FIG. 11 shows the articles of FIGS. 10A and 10B assembled and particularly showing the laparoscopic conduit trapped in the access valve of the laparoscopic port sheath of FIG. 10A;

DETAILED DESCRIPTION

Figure 9:
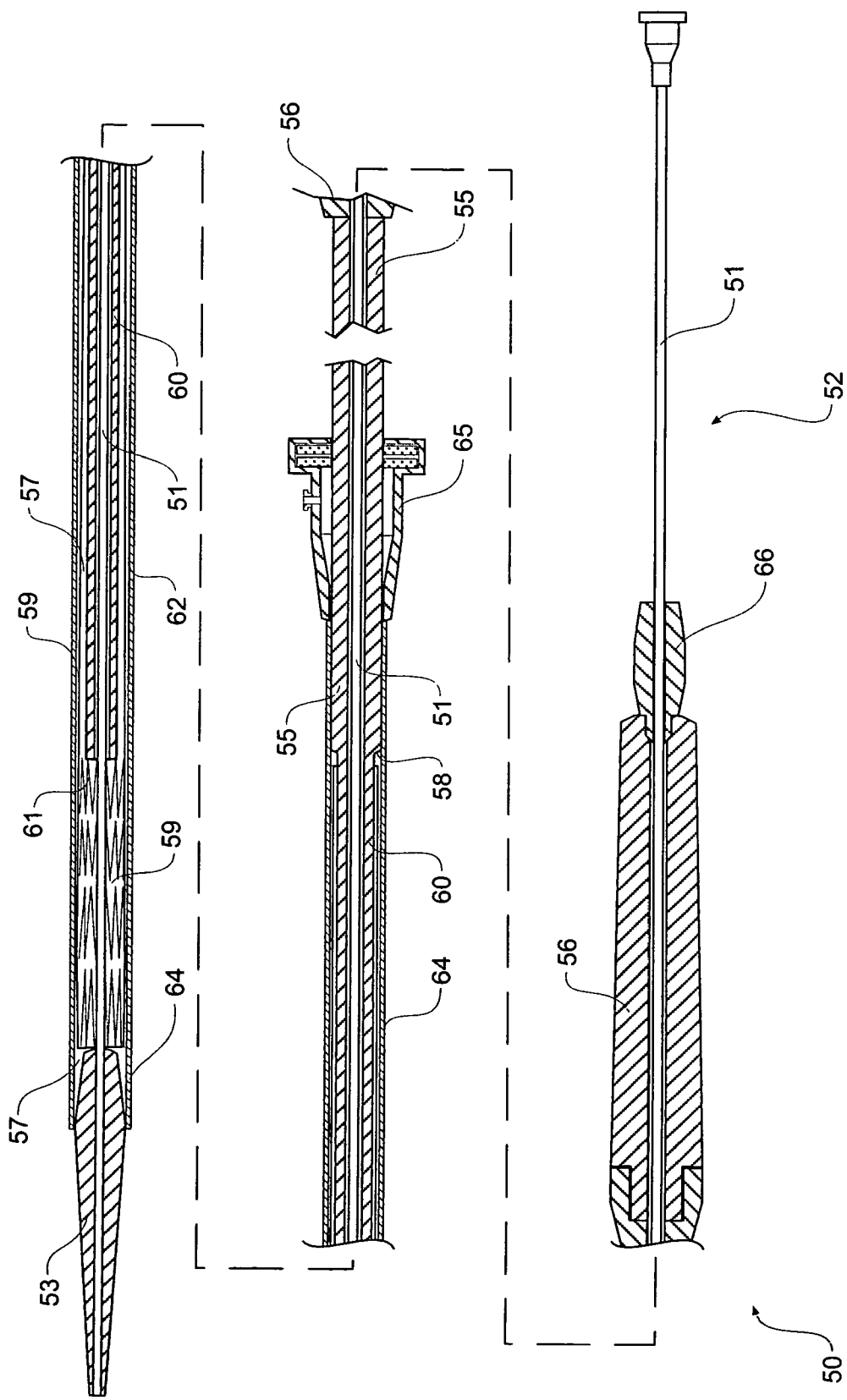
FIG. 9 shows a deployment device or introducer suitable for deploying the laparoscopic conduit of the type shown in FIGS. 1 to 4.

Now looking more closely to the drawings, and in particular FIG. 1, it will be seen that the laparoscopic conduit 1 according to one embodiment of the present invention comprises a elongate biocompatible graft material tube 2 which has a stented proximal portion 3 and an elongate unstented distal portion 4. There are four stents 5a to 5d in the proximal stented portion 3 with wide gaps 6 between the first and second stents 5a and 5b and second and third stents 5b and 5c from the proximal end 7 and a narrow gap 8 between the third and fourth stents 5c and 5d. In a preferred embodiment the tube has a diameter of 10 mm, the stents are 17 to 22 mm long each and the wider gaps are 3 mm and the narrower gap is 1 mm. The laparoscopic conduit 1 may have an overall length of about 400 mm.

When deployed, the laparoscopic conduit 1 fits into a vessel of the human or animal body with the wall of the vessel being received in one of the gaps 6 with the stents either side acting to seal the graft material into the aperture.

FIG. 2 shows a similar embodiment of laparoscopic conduit to that shown in FIG. 1 except that the laparoscopic conduit 10 has an enlarged proximal end 11 which tapers down to the diameter of the elongate unstented portion 12. This embodiment of laparoscopic conduit is adapted to be fitted into a relatively narrow vessel such as the iliac artery and the unstented portion 12 attached further down the iliac artery or across to the contralateral iliac artery to provide a bypass. In a preferred embodiment the tube has a diameter of 12 mm at the proximal end and after the first stent it tapers down to 8 mm and the unstented portion has a diameter of 8 mm, the stents are 17 to 22 mm long each and the wider gaps are 3 mm and the narrower gap is 1 mm. The laparoscopic conduit may have an overall length of about 400 mm.

FIG. 3 shows a similar tapered version of a laparoscopic conduit 15 except that the distal end 16 is larger so that it can be deployed into a larger vessel such as an aorta and the unstented portion 17 can be extended to act as a bypass to, for instance, a common iliac artery. In a preferred embodiment the tube has a diameter of 40 mm at the proximal end and after the first stent 18 it tapers down to 20 mm and the unstented portion has a diameter of 20 mm, the stents are 17 to 22 mm long each and the wider gaps 19a are 3 mm and the narrower gap 19b is 1 mm. The laparoscopic conduit may have an overall length of about 400 mm.

FIG. 4 shows a similar embodiment of laparoscopic conduit to that shown in FIG. 2 except that the laparoscopic conduit 20 includes for its unstented portion 21 a corrugated graft material which may provide better support for a vascular bypass. In a preferred embodiment the tube has a diameter of 12 mm at the proximal end and after the first stent it tapers down to 8 mm and the corrugated unstented portion has a diameter of 8 mm and a length of about 300 mm, the stents 23 are 17 to 22 mm long each and the wider gaps 24a are 3 mm and the narrower gap 24b is 1 mm. The laparoscopic conduit may have an overall length of about 400 mm.

FIG. 5 shows a long, sharp, tapered obturator 30 suitable for the present invention. This obturator is used to gain vascular access as will be discussed in relation to FIGS. 20 to 24. The elongate obturator has an elongate cylindrical body, a tapered proximal end 31 and a guide wire lumen 32 through the body. The obturator is shown partly in cutaway view to show the guide wire lumen. Preferably the long obturator has a length of about 450 mm.

FIG. 6 shows a short, tapered obturator 35. This obturator 35 has an elongate cylindrical body, a tapered proximal end 36 and a guide wire lumen 37 through the body. The obturator is shown partly in cutaway view to show the guide wire lumen. Preferably the short obturator has a length of about 250 mm.

FIG. 7 shows a blunt obturator 38 which has a blunt proximal end 39. This blunt obturator is used for pushing through the abdominal wall in an initial stage of the laparoscopic procedure. Preferably the blunt obturator has a length of about 450 mm.

FIG. 8A shows one embodiment of a long, curved needle 40 suitable for passing through the laparoscopic port sheath after it has been deployed through the abdominal wall as will be discussed in relation to FIGS. 13 and 21. The curved needle 40 has a curved proximal end 41 with a sharpened tip 42 and a lumen 43 through it of sufficient size to pass a guide wire through once access has been made into a vessel using the tip 42. The needle is shown partly in cutaway view to show the guide wire lumen. Preferably the elongate curved needle is an 18 gauge needle with a lumen sufficient for a 0.035" (0.9 mm) guide wire and has a length of about 320 mm. Alternatively the lumen of the needle may have a diameter in the range of 0.014" to 0.038" (0.35 mm to 1 mm) to enable it to be used with all guide wires that could be potentially be used.

FIG. 8B shows an alternative embodiment of a long, curved needle 44 suitable for passing through the laparoscopic port sheath after it has been deployed through the abdominal wall as will be discussed in relation to FIGS. 13 and 21. The curved needle 44 has a reinforcing body 46 around a catheter 45 with a curved proximal end 48 with a sharpened tip 49 and a lumen 47 through it of sufficient size to pass a guide wire through once access has been made into a vessel using the tip 42. The curved needle 44 is shown partly in cutaway view to show the catheter 45 within the reinforced body and the guide wire lumen 47 through the catheter. The reinforcing body 46 extends along most of the needle and may terminate about 2 cm short of the tip and have a tapered proximal end. The reinforcing assists in providing rigidity to the needle when it is being forced into the aorta or other artery as shown in FIGS. 13 and 21. Preferably the elongate curved needle is an 18 gauge needle with a lumen sufficient for a 0.035" (0.9 mm) guide wire and has a length of about 320 mm. The reinforcing can give an outside diameter of about 3 mm. Alternatively the lumen of the needle may have a diameter in the range of 0.014" to 0.038" (0.35 mm to 1 mm) to enable it to be used with all guide wires that could be potentially be used.

FIG. 9 shows a deployment device for a laparoscopic conduit of the present invention. The introducer 50 comprises a guide wire catheter 51 which extends from a distal end 52 to and through a proximal nose cone dilator 53. The guide wire catheter allow the deployment device to be deployed over a pre-placed guide wire. A pusher catheter 55 extends from a handle 56 to an annular region 57 distal of the nose cone dilator 53 into which the laparoscopic conduit 59 of the type shown in FIGS. 1 to 4 is received. Proximally of the proximal end 58 of the pusher catheter 55 is a pusher catheter extension 60 which is of lesser diameter than the pusher catheter 55 and extends forward to the distal-most stent 61 of the laparoscopic conduit 59. The unstented portion 62 of the laparoscopic conduit 59 extends coaxially around the pusher catheter extension 60 essentially back to the proximal end 59 of the pusher catheter 55. A sheath 64 extends from the nose cone dilator 53 back to a sheath manipulator 65 on the pusher catheter 55. The sheath 64 retains the laparoscopic conduit 59 in a retained condition around the guide wire catheter 51 and the pusher catheter extension 60 until the sheath is withdrawn to release the laparoscopic conduit. The sheath 64 is withdrawn by moving the sheath manipulator 65 to which it is joined in a distal direction along the pusher catheter 55 towards the handle 56.

Once the laparoscopic conduit 59 has been released from the deployment device, pin vice 66 can be released to enable the guide wire catheter 51 to be moved distally which moves the nose cone dilator 53 back towards the pusher catheter extension and the sheath can be moved forward to the nose cone dilator 53 before the introducer 50 is withdrawn.

FIG. 10A shows a laparoscopic port sheath according to one embodiment of the invention. The laparoscopic port sheath 70 according to this embodiment comprises an elongate sheath 71 which in use is adapted to pass through the abdominal wall as will be discussed later. At the distal end 72 of the laparoscopic port sheath is an access valve arrangement 73. This access valve 73 is of the automatically closing type which includes a silicone disc 73a with a crossed slit or two silicone discs with a slit in each with the slits at right angles. The sheath preferably has a length of about 250 mm and an internal diameter of 24 French and the laparoscopic port sheath has an overall length of 325 mm.

FIG. 10B shows a second access sheath 80 loaded with a short obturator 82. The short obturator 82 has a guide wire lumen 83. The second access sheath 80 has a sheath 84 mounted to the access port body 85. The access port has a first seal arrangement 86 and a second arrangement 87. The valve 86 is of the silicone crossed slit type as in FIG. 10A and the valve 87 is a manually operable valve which can be rotated to seal the valve around as small an object as a guide wire. The sheath preferably has a length of about 60 mm and an internal diameter of 22 French and the second access sheath has an overall length of 325 mm.

FIG. 10C shows a third access sheath 75. The third access sheath 75 has a sheath 76 mounted to the access port body 85. The access port has a first valve arrangement 77 and a second valve arrangement 78. The valve 77 is of the silicone crossed slit type as in FIG. 10A and the valve 78 is a manually operable valve which can be rotated to seal the valve around as small an object as a guide wire. The third sheath preferably has a length of about 350 to 400 mm and an internal diameter of 22 French and the third access sheath has an overall length of up to 500 mm. The third access sheath 75 can be used as an alternative to the first access sheath 70.

FIG. 11 shows the laparoscopic port sheath 70 of FIG. 10A with a laparoscopic conduit 90 of the type shown in FIG. 1, for instance, extending out of the sheath 71 and through the seal 73 in the body 74 to extend distally from the laparoscopic port sheath 72. A shorter second access sheath 80 of FIG. 10B has been deployed into the rear 72 of the laparoscopic access port 70 with the obturator 82 in position such that the sheath 84 is sealed into the valve 73 with the laparoscopic conduit 90 trapped between them. The short tapered obturator 82 has then been withdrawn and the valve 87 closed.

FIGS. 12 to 19 show the process of providing a laparoscopic access port according to the present invention. In this embodiment the access includes the placement of a laparoscopic conduit which can subsequently be used to bypass for instance an occluded or tortuous portion of the iliac artery or to provide a contra-iliac bypass.

Figure 12:
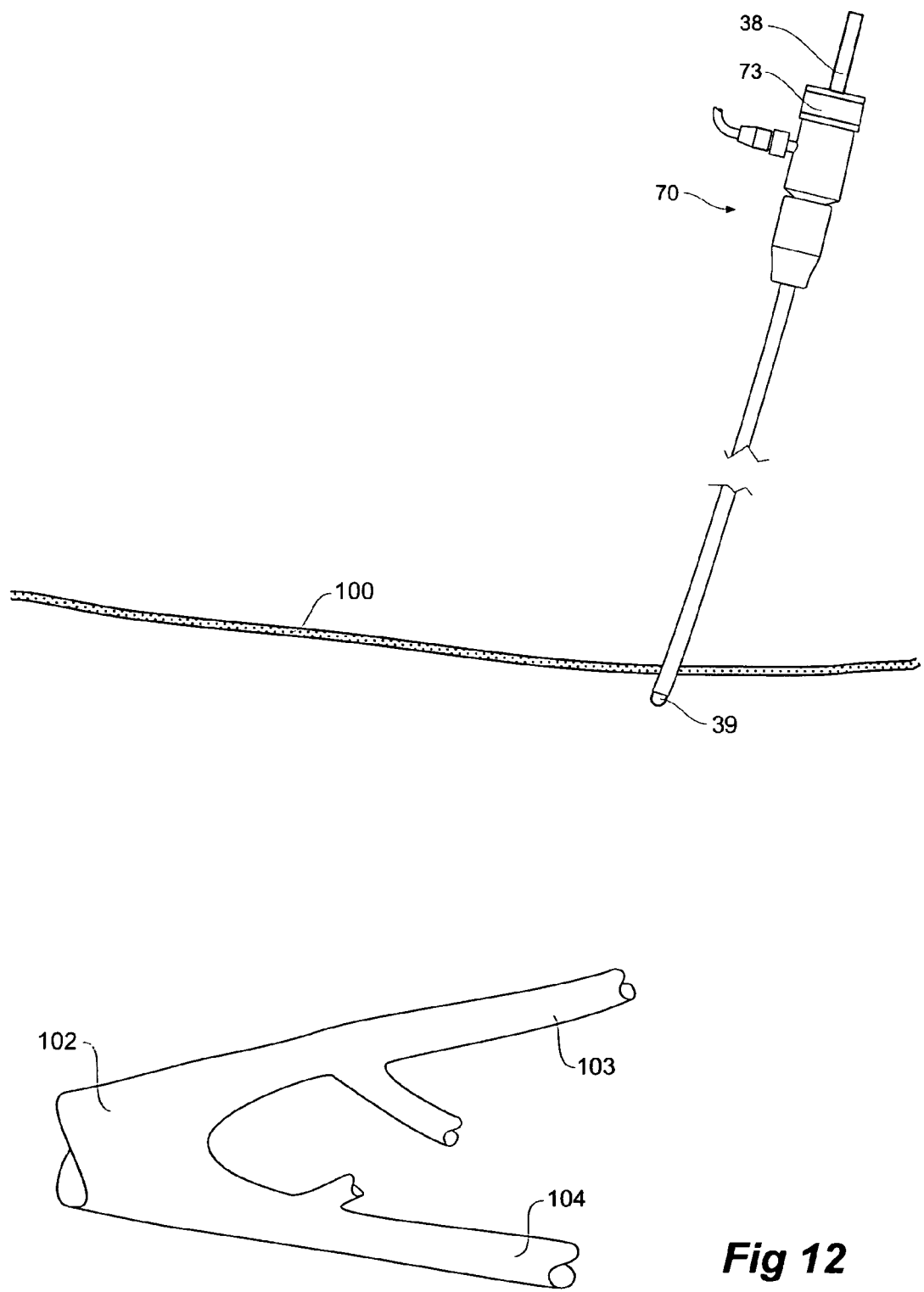
FIGS. 12 to 20 show various stages of installation of one embodiment of a vascular access arrangement using a laparoscopic port sheath and laparoscopic conduit according to one embodiment of the present invention.

In FIG. 12 there is shown schematically an abdominal wall 100 and an aorta 102 splitting into iliac arteries 103 and 104. It is the object of this process to place a laparoscopic port sheath through the abdominal wall to deploy a laparoscopic conduit into the iliac artery 103.

In FIG. 12 a nick has been made into the abdominal wall 100 and the laparoscopic port sheath 70 (See FIG. 10A) with the blunt obturator (See FIG. 7) loaded into it has been pushed through the muscle of the abdominal wall 100. The muscle of the abdominal wall provides a convenient seal at the access point around the sheath. The laparoscopic port sheath 70 is then advanced towards the iliac artery and the blunt obturator 38 withdrawn. At this stage the seal 73 in the rear 72 of the laparoscopic port sheath 70 prevents loss of insufflation pressure within the abdominal cavity.

Figure 13:
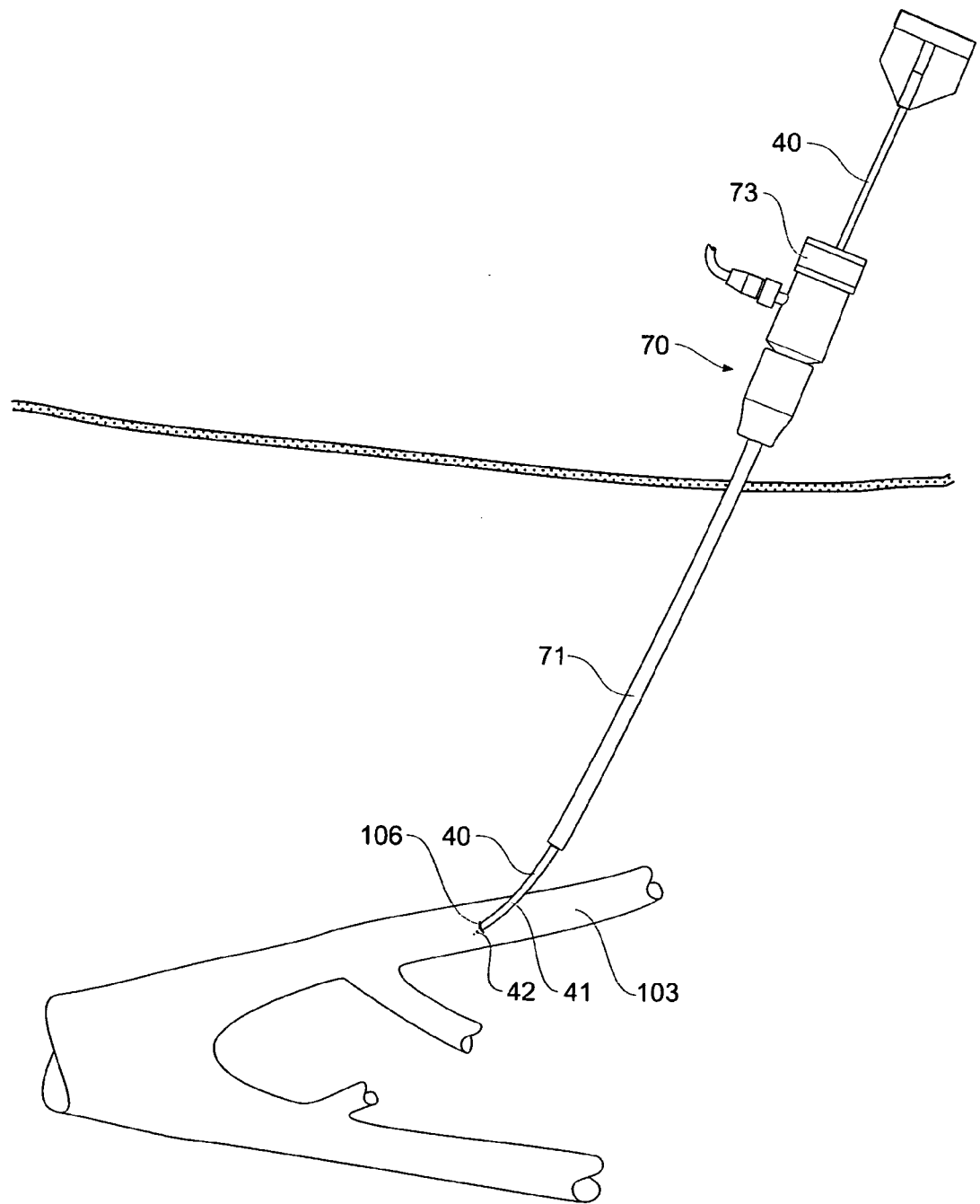

As shown in FIG. 13 the laparoscopic port sheath 70 has been advanced towards the iliac artery 103 and the curved needle 40 (see FIG. 8A) has been inserted through the valve 73 and down the sheath 71 until it extends out of the proximal end of the sheath 71. The tip 42 of the needle 40 can then be inserted through the wall of the iliac artery 103 using radiographic guidance to form an aperture 106. The curve 41 ensures that the tip of the needle can then be progressed proximally into the artery 103. Successfully penetration of the aorta will be indicated by blood flow emanating from the distal end of the needle 40.

Figure 14:
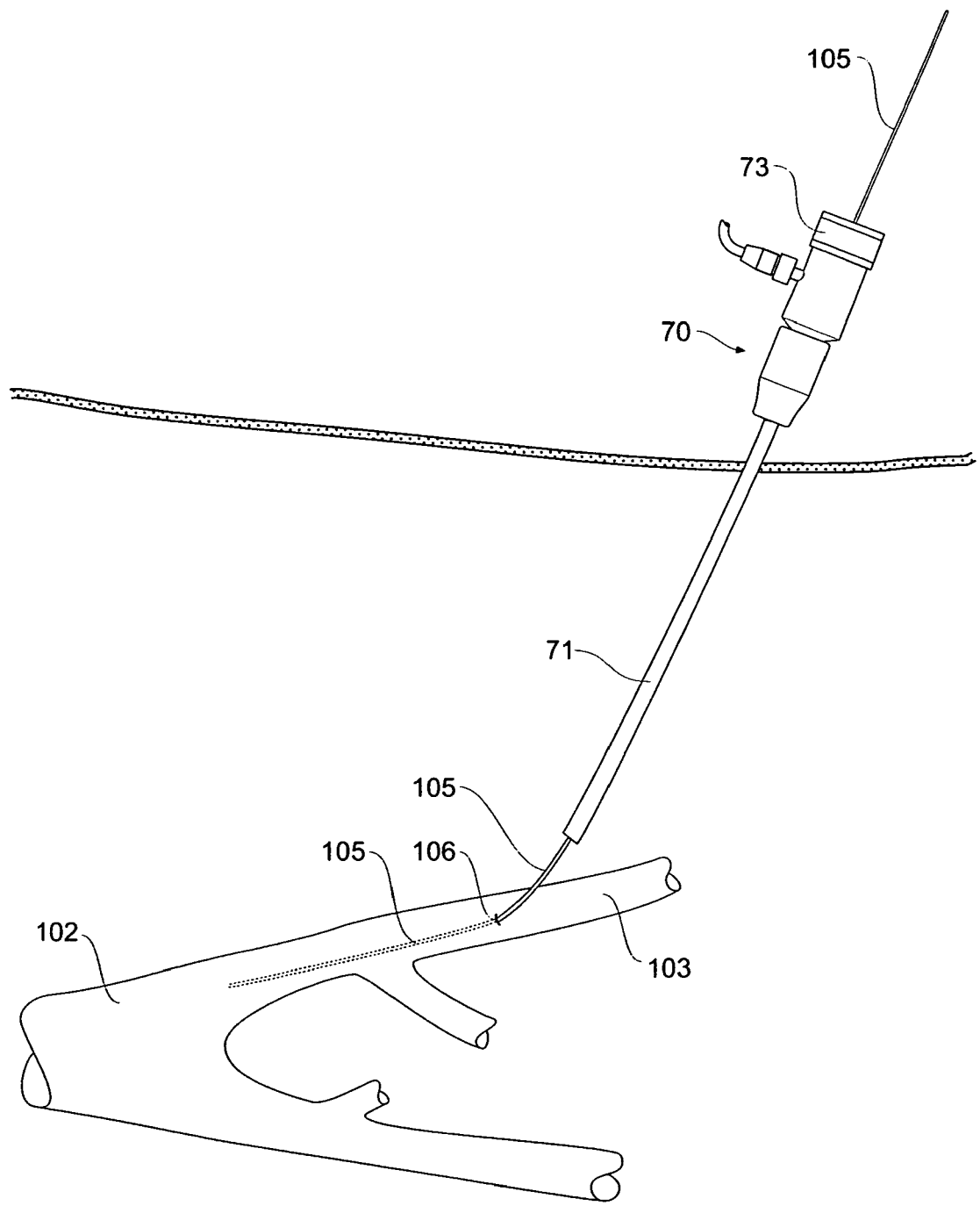

A guide wire 105 is then passed through the needle to enter into the iliac artery and extend proximally and the needle is then withdrawn leaving the guide wire in place as shown in FIG. 14. Hence the guide wire 105 passes through the laparoscopic access sheath 70 with sealing at the valve 73 and then into the iliac artery 103 through the aperture 106 and extending towards the aortic bifurcation and the aorta 102.

At this stage the guide wire can be replaced by a stiffer guide wire if desired. This can be done by deploying a thin walled catheter over the guide wire and into the artery, removing the first guide wire, extending the stiffer guide wire through the thin walled catheter and into the artery and then removing the thin walled catheter leaving the stiffer guide wire in place.

Figure 15:
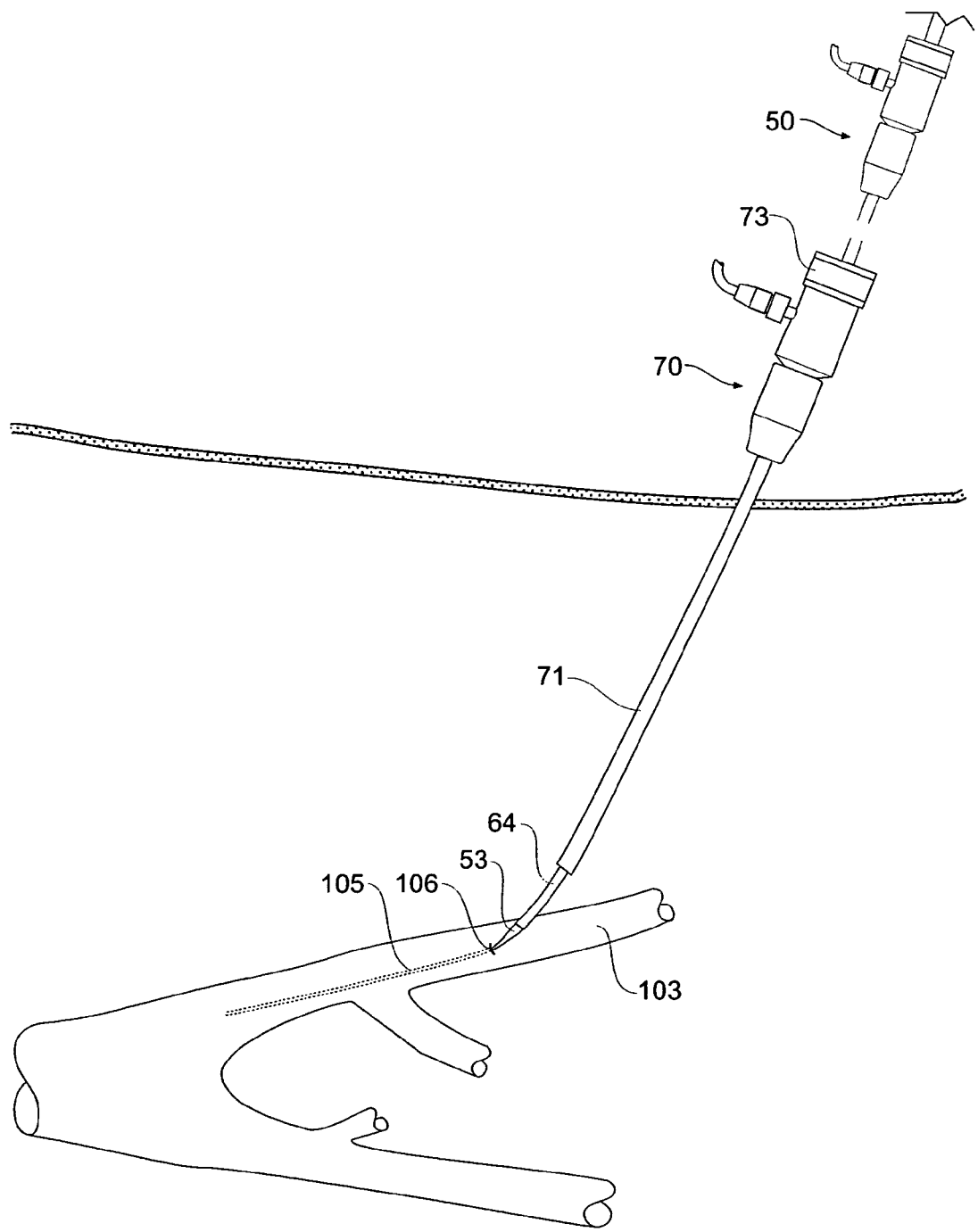
Figure 16:
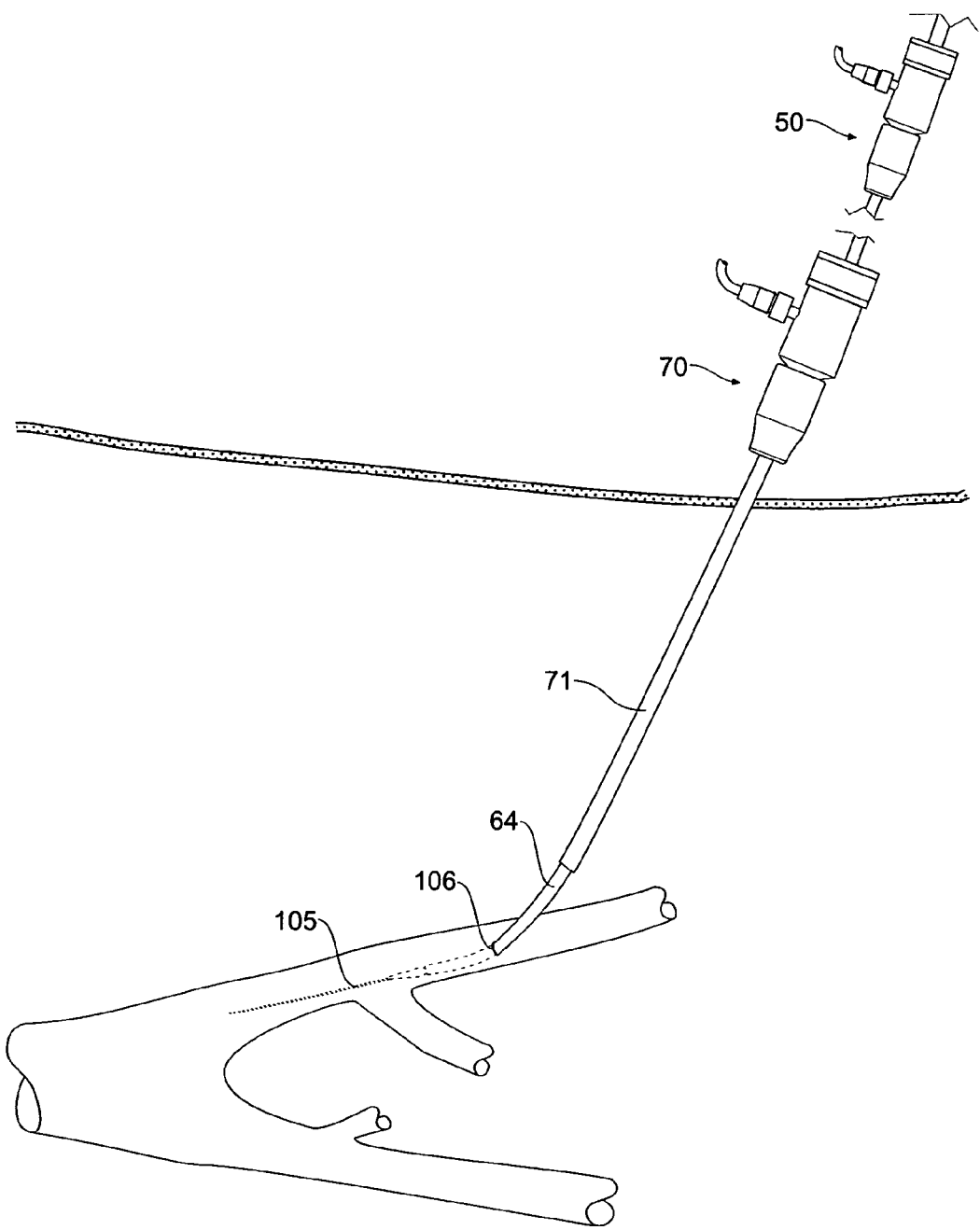
Figure 17:
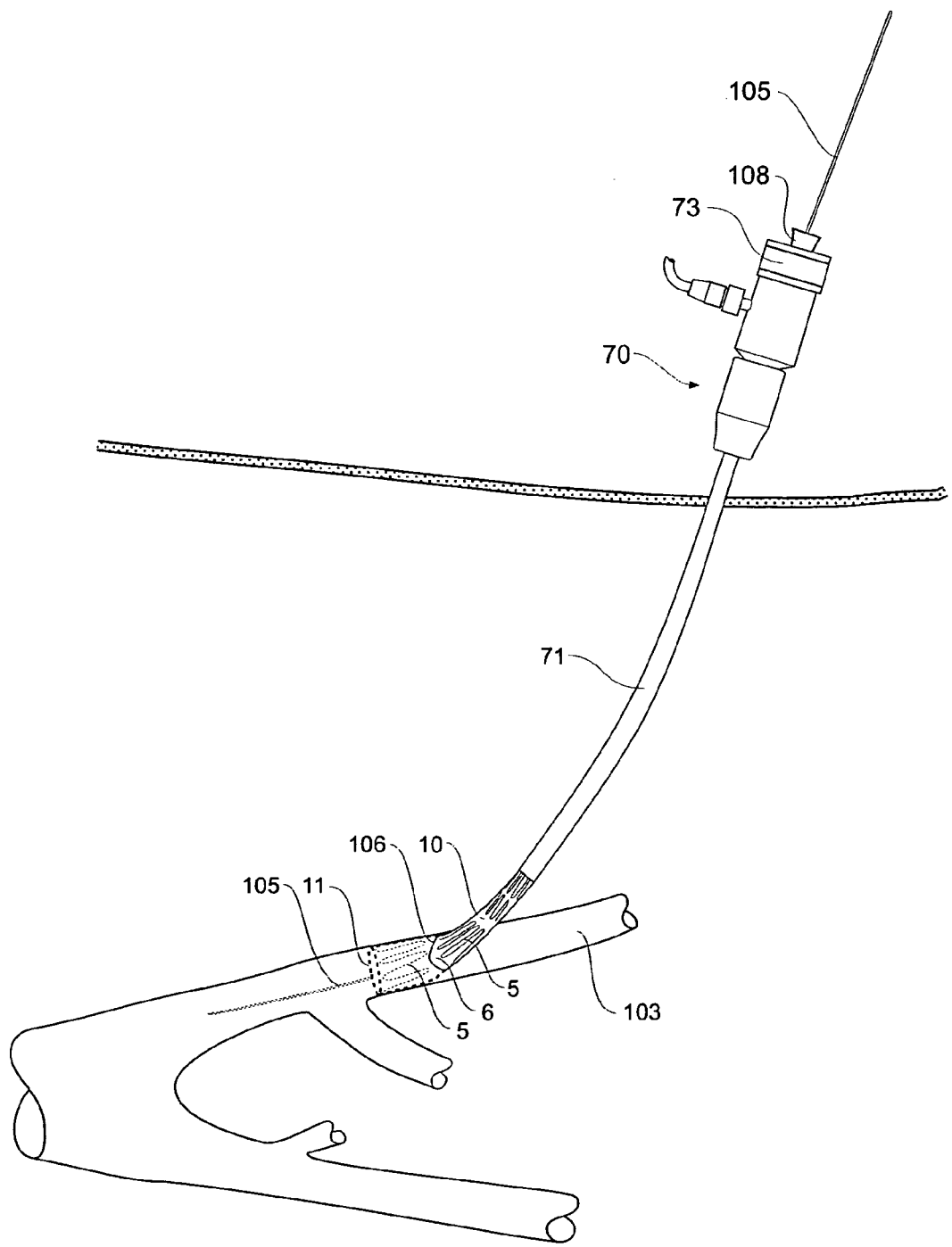

In the next stage as shown in FIG. 15 a laparoscopic conduit deployment device 50 of the type shown in FIG. 9 is deployed through the seal 73 of the laparoscopic port sheath 70 and down the sheath 71 over the guide wire 105 until it reaches the aperture 106 in the iliac artery 103. The nose cone dilator 53 on the proximal end of the deployment device 50 then creates a larger aperture in the iliac wall into which the nose cone dilator and the sheath 64 of the deployment device 53 can pass. This stage is shown in FIG. 16. The aperture or slit 106 is now large enough to have the sheath 64 pass through it but natural resiliency provides a suitable seal around the sheath 64.

In the next stage the sheath 64 of the deployment device 52 is with drawn to deploy the laparoscopic conduit 10 for instance of the type shown in FIG. 2.

As deployed the aperture 106 in the wall of the iliac artery 103 is positioned in the gap 6 between the first and second stents 5. These self-expanding stents provide a resilient pressure which keeps the seal around the aperture. The proximal end 11 of the laparoscopic conduit is sized to seal on the inside of the aorta 103. The deployment device 52 is then withdrawn leaving the distal end 108 of the laparoscopic conduit 10 extending out of the seal 73 of the laparoscopic port sheath 70. The guide wire 105 still remains extending through the laparoscopic conduit 10 and laparoscopic port sheath 70. This is the situation shown in FIG. 17.

Figure 18:
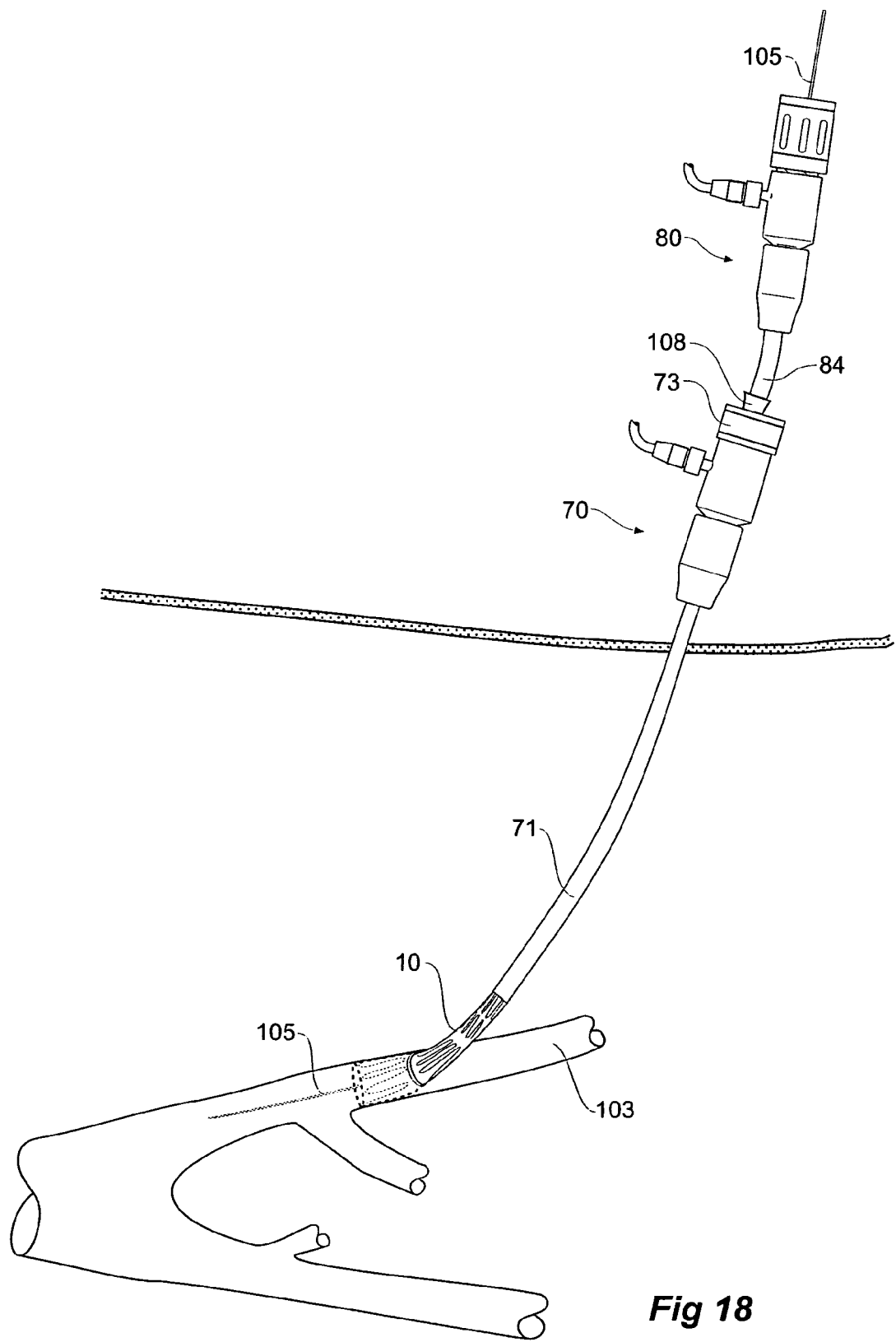

In the next stage as shown in FIG. 18 the second access sheath 80 and valves 86 and 87 with the shorter tapered obturator 82 loaded into is inserted into the valve 73 so that its sheath 84 fits inside the distal end 108 of the laparoscopic conduit 10 and provides a seal in the valve 73. This is the situation as shown in longitudinal cross-section in FIG. 11.

The short tapered obturator 82 can then be removed and the manually operable valve 87 closed around the guide wire 105.

Various endovascular deployment processes can then be used effectively through the valve 87 and the sheath 71 and laparoscopic conduit 10 to place endovascular devices proximally of the iliac artery.

In one procedure for instance an aortouniliac device may be placed extending up into the aorta and down into the iliac artery 103. Alternatively a device may be placed in other portions of the vascular such as up into the infrarenal and thoracic regions of the aorta.

Figure 19:
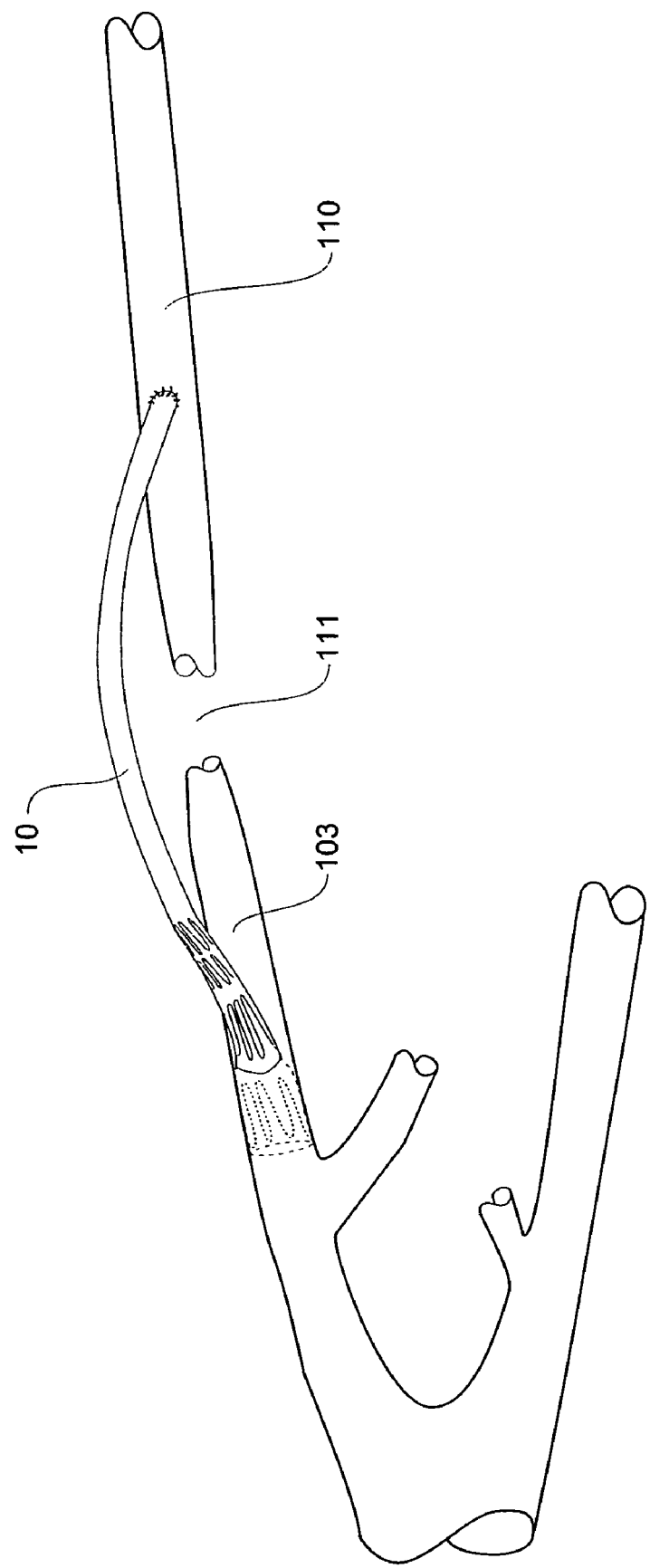

After all necessary procedures have been carried out the laparoscopic conduit can be removed by advancing the sheath 71 over the stents 5 on the laparoscopic conduit and with drawing the laparoscopic conduit with the laparoscopic port sheath. The aperture 106 can then be stitched shut using laparoscopic techniques or an occluder can be placed into the aperture. Alternatively the laparoscopic port sheath 70 can be removed and laparoscopic techniques used to stitch or fasten by other methods of fixation such as staples or rivets, the laparoscopic conduit 10 further down the iliac artery 110 or femoral artery to bypass an occlusion or convolution in the region 111 of the artery system. This situation is shown in FIG. 19.

FIGS. 21 to 24 show an alternative procedure according the present invention in which an temporary sheath is placed into the vascular for deployment of endovascular devices directly into the vascular after which the laparoscopic port sheath is removed.

Figure 20:
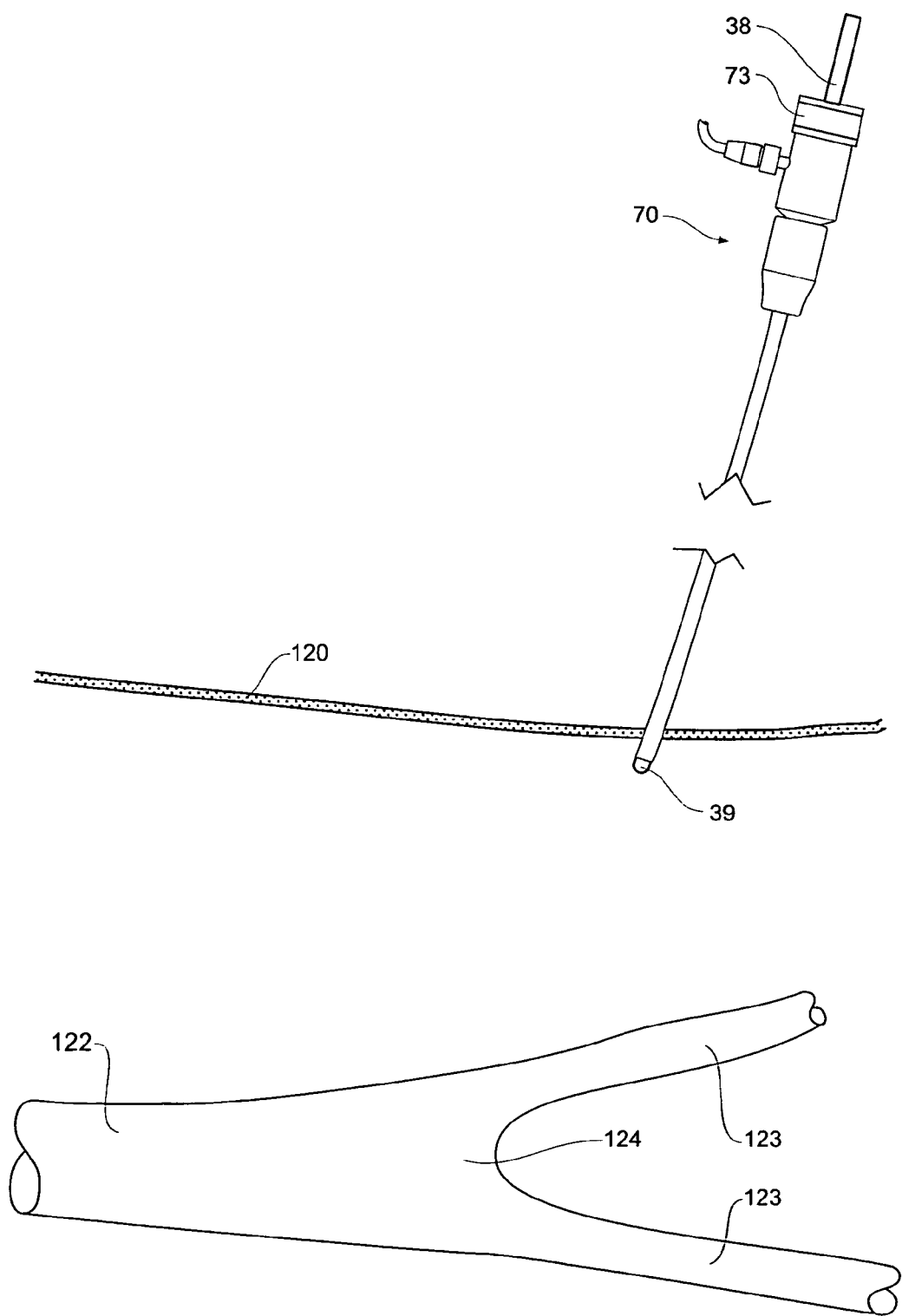

FIG. 20 shows a schematic view of a portion of a human or animal body including an abdominal wall 120 and an aorta 122 with iliac arteries 123 extending from an aortic bifurcation 124. A laparoscopic port sheath 70 of the type shown in FIG. 10A and loaded with a blunt obturator 38 of type shown in FIG. 7 has been deployed so that the blunt end 39 passes through a cut or nick made in the abdominal wall.

Figure 21:
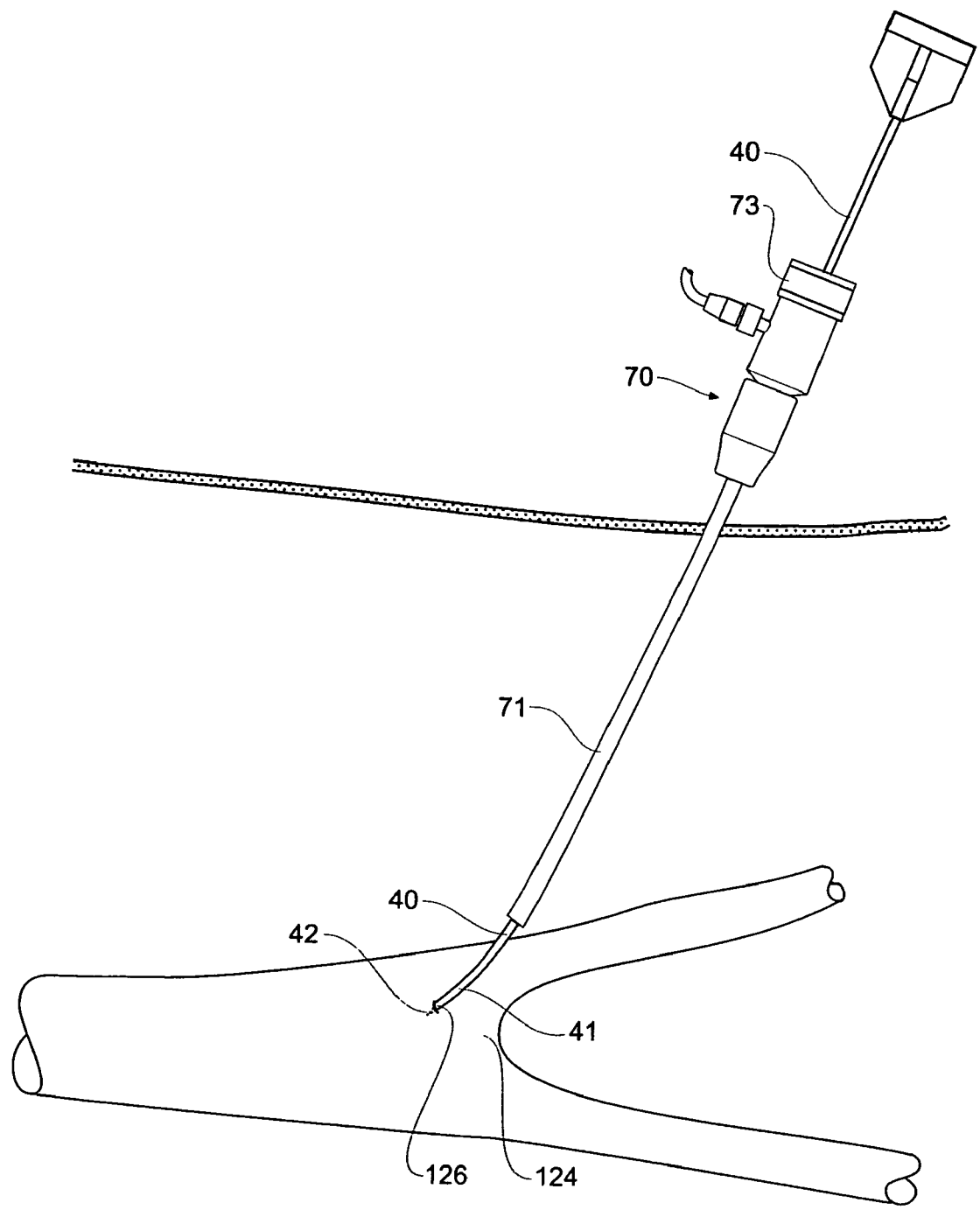
FIGS. 21 to 24 show the various stages of deploying a temporary laparoscopic vascular access arrangement according to an embodiment of the present invention.
Figure 22:
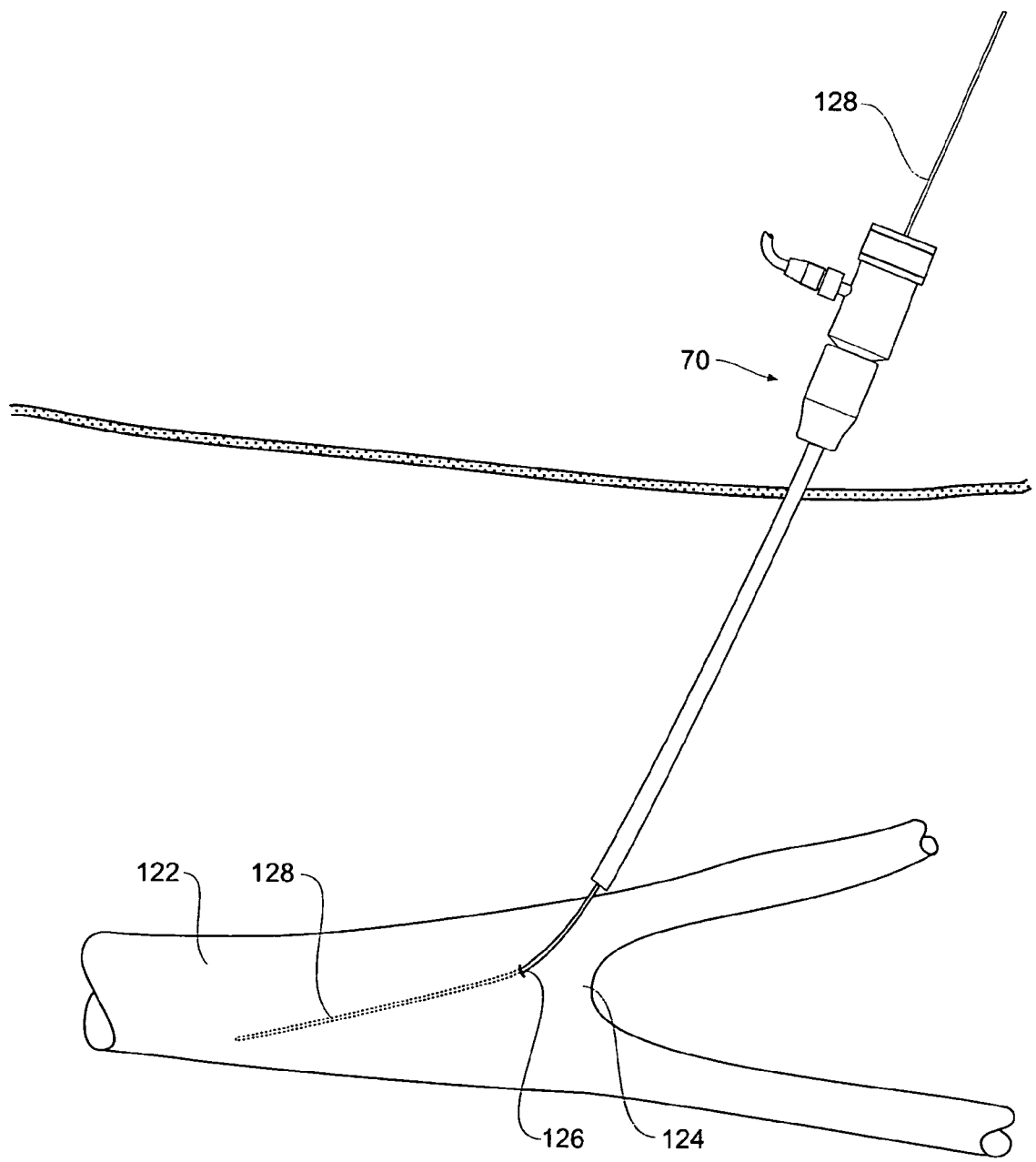
Figure 23:
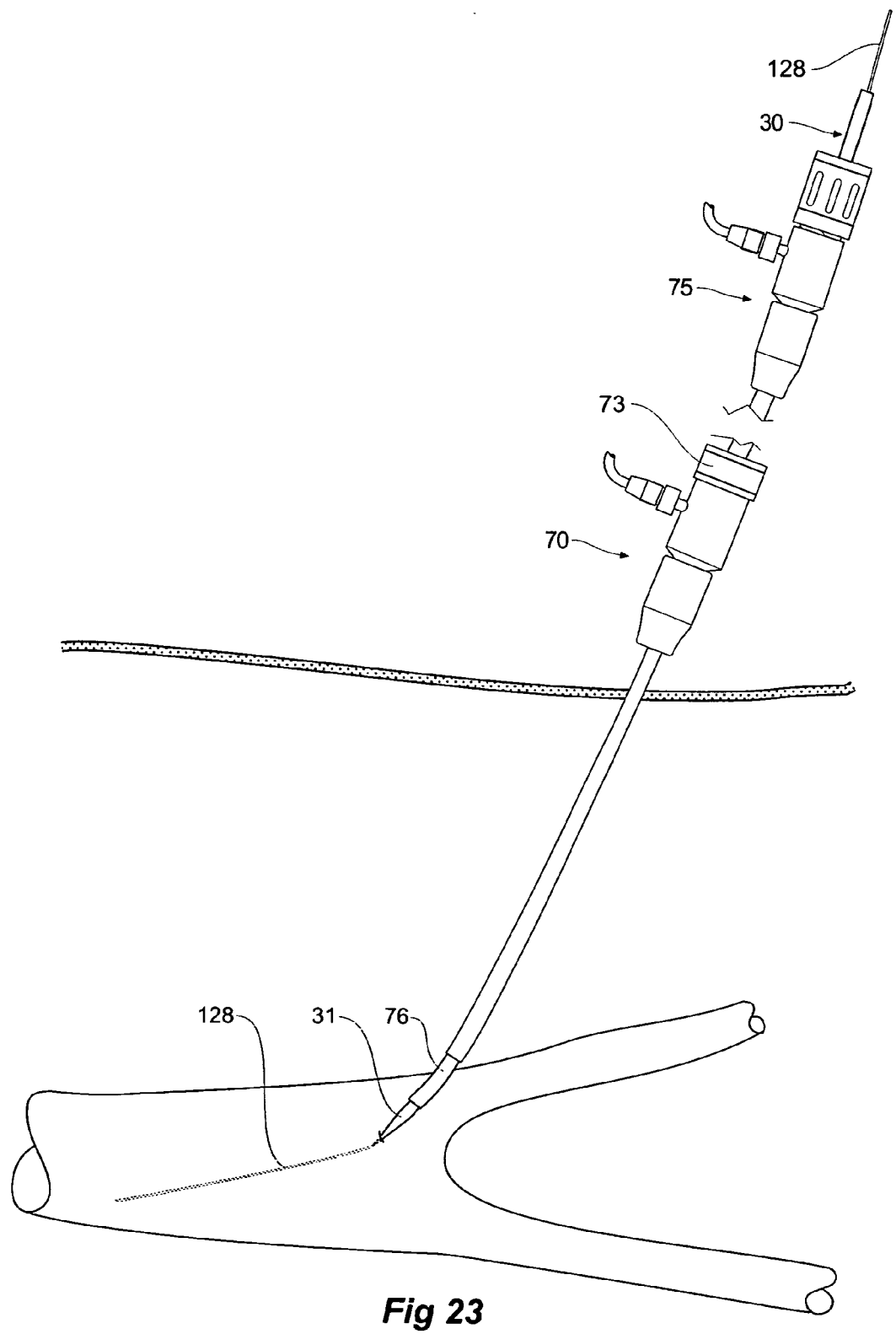

In FIG. 21 the laparoscopic port sheath 70 has been advanced so that its sheath 71 extends down towards the aortic bifurcation 124 and a curved needle 40 has been inserted through the access valve 73 and passed though the sheath 71 so that the curved end 41 extends out of the proximal end of the sheath 71. The sharpened tip 42 of the curved needle 40 is pushed into the aorta near the bifurcation to form a slit 126. Successfully penetration of the aorta will be indicated by blood flow emanating from the distal end of the needle 40. A guide wire 128 is then passed through the needle and the slit 126 so that it extends into the aorta and extends proximally through the aorta 122 and then the needle 40 is removed to give the situation as shown in FIG. 22.

At this stage the guide wire can be replaced by a stiffer guide wire if desired. This can be done by deploying a thin walled catheter over the guide wire and into the artery, removing the first guide wire, extending the stiffer guide wire through the thin walled catheter and into the artery and then removing the thin walled catheter leaving the stiffer guide wire in place.

Figure 24:
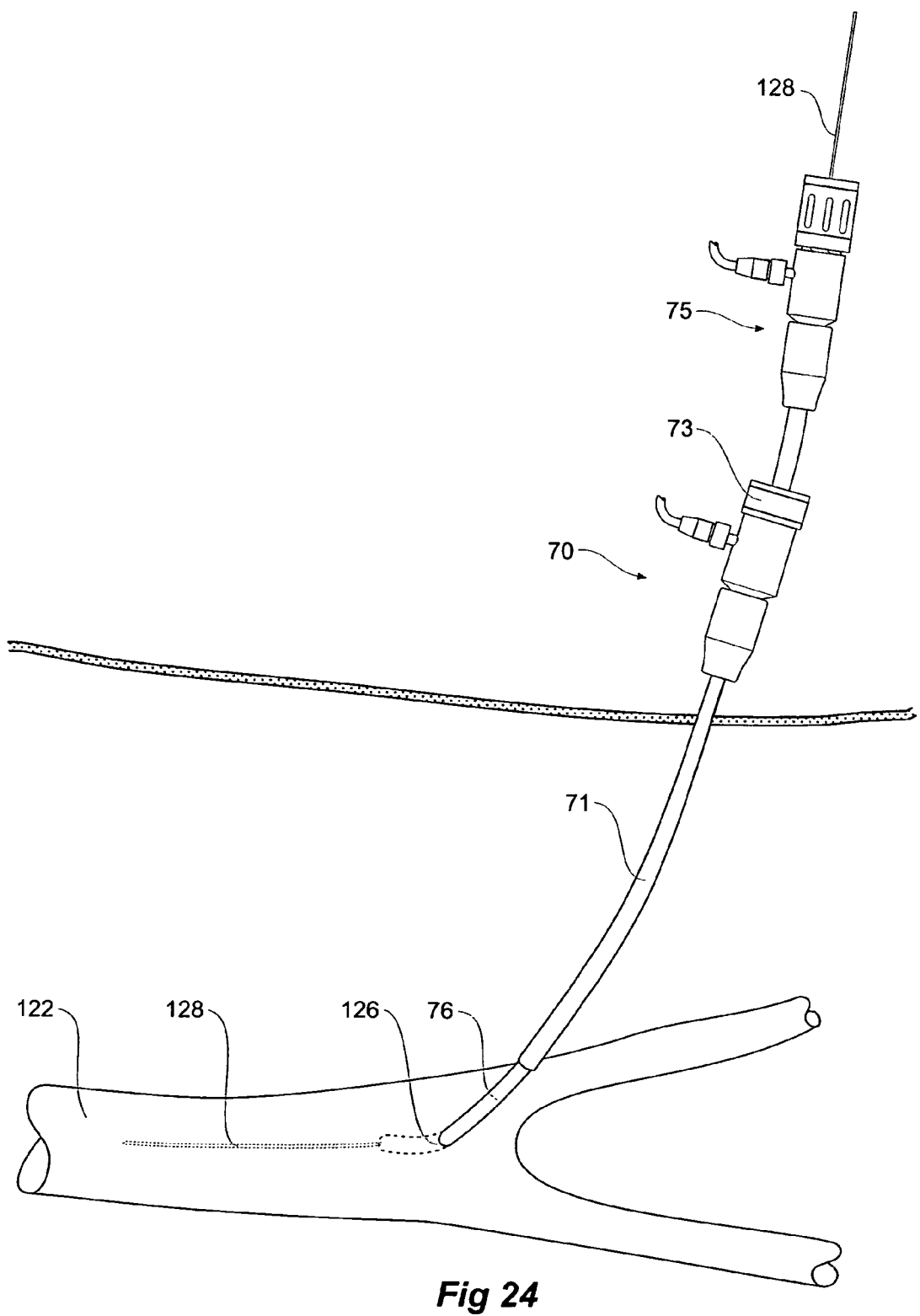

A further access sheath 75 with a valve at the distal end of the type shown in FIG. 10C which is loaded with an obturator 30 with a tapered tip 31 can then be extended through the valve 73 of the laparoscopic access port sheath 70 so that its sheath 76 with obturator taper 31 extending from the sheath 76 can then be passed over the guide wire 128 to enter the slit 126 so that sheath 76 enters the aorta 122. The obturator 30 can then be withdrawn to leave the position as shown in FIG. 24. The guide wire 128 may be replaced at this stage with a stiffer guide wire and the guide wire extended proximally through the aorta 122 so that a deployment device for an endovascular stent graft may be deployed over the guide wire 128. When all access has been completed the sheath 71 on the laparoscopic port sheath 70 can be withdrawn and the access port 80 also withdrawn and the slit 126 sewn up or an occluder placed into it.

Kit of Parts for Temporary Option
1. Curved hollow needle
2. Guide wire.
3. Laparoscopic port and sheath with blunt obturator loaded into it.
4. Smaller diameter sheath with sharp ended obturator loaded into it.
5. Optionally a stiffer guide wire and thin walled catheter Preferred Method of Operation for the Temporary Option
1. Make a small nick in the abdomen wall at the desired entry point.
2. Introduce laparoscopic port sheath with longer blunt obturator loaded into it through the nick and extend internally to adjacent the aortic bifurcation or just down one of the iliac arteries. Withdraw the obturator.
3. Insert the curved needle through the first access valve and the laparoscopic port sheath and puncture the vessel at the desired point.
4. Extend a guide wire through the needle and into the artery.
5. Remove the curved needle.
6. Optionally replace the guide wire with a stiffer guide wire. This can be done by deploying a thin walled catheter over the guide wire and into the artery, removing the first guide wire, extending the stiffer guide wire through the thin walled catheter and into the artery and then removing the thin walled catheter leaving the stiffer guide wire in place.
7. Deploy the smaller diameter sheath with sharp ended obturator loaded into it over the guide wire and into the vessel and extending proximally in the vessel.
8. Withdraw the obturator.
9. Access through the valve on the smaller diameter sheath can then be used for access through the smaller diameter sheath into the vasculature for endovascular introduction techniques proximal of the insertion point.
10. Deploy a sealing plug through the smaller diameter sheath into aperture in vessel wall and remove smaller diameter sheath and stitch up aperture on abdominal wall. Alternatively the slit in the vessel can be stitched over using laparoscopic surgical techniques or an occluder placed into the aperture.

Kit of Parts for the Bypass Option
1. Curved hollow needle.
2. Guide wire.
3. Laparoscopic port sheath with longer blunt obturator loaded into it.
4. Shorter sheath with shorter obturator loaded into it.
5. Long sharp obturator
6. Laparoscopic conduit loaded onto a endovascular delivery device
7. Optionally a stiffer guide wire and thin walled catheter Preferred Method of Operation for the Bypass Option
1. Make a small nick in the abdomen wall at the desired entry point.
2. Introduce laparoscopic port sheath with longer blunt obturator loaded into it through the nick and extend internally to adjacent the aortic bifurcation or just down one of the iliac arteries. Withdraw the obturator.
3. Insert the curved needle with guide wire loaded into it through the first access valve and the Laparoscopic port sheath and puncture the vessel at the desired point.
4. Extend guide wire through the needle and into the artery.
5. Remove the curved needle.
6. Optionally replace the guide wire with a stiffer guide wire. This can be done by deploying a thin walled catheter over the guide wire and into the artery, removing the first guide wire, extending the stiffer guide wire through the thin walled catheter and into the artery and then removing the thin walled catheter leaving the stiffer guide wire in place.
7. Deploy the laparoscopic conduit loaded onto an endovascular delivery device through the Laparoscopic port sheath and over the guide wire and into the vessel and extending proximally in the vessel. The nose cone on the endovascular delivery device acting as a obturator to open up the vessel aperture.
8. Release the laparoscopic conduit by withdrawing the sheath of the endovascular delivery device. Distal end of conduit extends out of first access valve. Conduit is preferably positioned so that the wall of the vessel is at the gap between the first and second stents or the second and third stents.
9. Deploy the shorter sheath with shorter obturator loaded into it over the guide wire and into the distal end of the conduit and into the first access valve. Remove the shorter obturator. Captor™ valve on shorter sheath is closed when obturator removed.
10. Access through the Captor™ valve on the shorter sheath can then be used for access through the conduit into the vasculature for endovascular introduction techniques proximal of the insertion point.
11. After use the conduit can either be removed or used as a bypass to another vessel.

(a) Removed by advancement of the longer sheath to re-enter the vessel and the internal self expanding stents on the conduit withdrawn back into the sheath as it is advanced. Entire device withdrawn and then the slit in the vessel stitched over using laparoscopic surgical techniques or an occluder placed into the aperture.

(b) Distal end of conduit stitched to another vessel such as a femoral bypass or to bypass a damaged portion of vessel using laparoscopic surgical techniques.

(c) Distal end of conduit is occluded and left in abdominal cavity.

What is claimed is:

1. A laparoscopic deployment device in combination with a laparoscopic conduit, the laparoscopic conduit comprising, an elongate graft tube comprising a proximal end and a distal end, the proximal end comprising at least two self expanding stents affixed thereto to keep the proximal end of the elongate graft tube open in use, there being a gap between the at least two stents to provide a sealing region to seal through an aperture in a vessel wall, the at least two self expanding stents including a distal most stent that is further from the proximal end of the elongate graft tube than the other of the at least two self expanding stents, and the elongate graft tube comprising an elongate distal unstented portion, the deployment device comprising, a pusher catheter comprising a proximal end, a guide wire catheter extending from the pusher catheter to a nose cone dilator, the nose cone dilator comprising a distal end, and a pusher catheter extension being of lesser diameter than the pusher catheter, the pusher catheter extension extending from the proximal end of the pusher catheter, a sheath extending from a sheath manipulator on the pusher catheter to the nose cone dilator thereby defining an annular space between the pusher catheter extension and the sheath, the laparoscopic conduit being mounted onto the delivery device whereby the pusher catheter extension extends proximally through the elongate distal unstented portion of the elongate graft tube in the annular space between the pusher catheter extension and the sheath, the pusher catheter extension bearing against the distal most stent and the proximal end of the laparoscopic conduit extending to the distal end of the nose cone dilator, the laparoscopic conduit being retained in a contracted condition by the sheath between the distal end of the nose cone dilator and the proximal end of the pusher catheter, whereby the pusher catheter extension bearing against the distal most stent on the laparoscopic conduit prevents distal movement of the laparoscopic conduit during retraction of the sheath during deployment of the laparoscopic conduit.

2. A laparoscopic deployment device in combination with a laparoscopic conduit as in claim 1 wherein the graft tube comprises four self expanding stents at the proximal end thereof, the self expanding stents comprising gaps therebetween, there being wider gaps between the first and second stents and the second and third stents and a narrower gap between the third and fourth stent and the pusher catheter extension bearing against the distal most of the four self expanding stents.

3. A laparoscopic deployment device in combination with a laparoscopic conduit as in claim 1 wherein the elongate distal unstented portion of the laparoscopic conduit comprises a corrugated biocompatible material portion.

4. A laparoscopic deployment device in combination with a laparoscopic conduit as in claim 1 wherein the graft tube has a diameter of from 12-40 mm in region of first stent, tapering to 6-20 mm in region of second stent and continuing at 6-20 mm diameter to the distal end.

5. A kit of parts for performing vascular access laparoscopically, the kit of parts comprising;
a laparoscopic deployment device in combination with a laparoscopic conduit as defined in claim 1, an elongate curved hollow needle, a guide wire, a laparoscopic port sheath, a blunt obturator of a diameter to extend through the laparoscopic port sheath, a smaller diameter sheath, and a sharp ended obturator of a diameter to extend through the smaller diameter sheath.

6. A kit of parts as in claim 5 wherein the laparoscopic port sheath comprises an elongate flexible sheath having a proximal end and a distal end and an access port at the distal end, the access port having a sealing valve therein and through which the laparoscopic deployment device can be advanced.

7. A kit of parts as in claim 5 wherein the smaller diameter sheath comprises an elongate flexible sheath having a proximal end and a distal end and an access port at the distal end, the access port having a self sealing valve and a manually operable valve therein.

8. A kit of parts as in claim 5 wherein the elongate curved hollow needle comprises a reinforcing body surrounding the needle.

* * * * *